United States Patent [19]

Shepherd

[11] Patent Number: 5,430,542
[45] Date of Patent: Jul. 4, 1995

[54] DISPOSABLE OPTICAL CUVETTE

[75] Inventor: A. P. Shepherd, San Antonio, Tex.

[73] Assignee: Avox Systems, Inc., San Antonio, Tex.

[21] Appl. No.: 867,031

[22] Filed: Apr. 10, 1992

[51] Int. Cl.⁶ .......................................... G01N 21/03
[52] U.S. Cl. .................................................. 350/246
[58] Field of Search .................................. 356/39, 246

[56] References Cited

U.S. PATENT DOCUMENTS

| | | | |
|---|---|---|---|
| Re. 28,801 | 5/1976 | Acker et al. | 356/246 |
| 3,690,836 | 6/1986 | Buissiere . | |
| 3,751,173 | 8/1973 | Sanz et al. | 356/246 |
| 4,088,448 | 5/1978 | Lilja et al. | 23/259 |
| 4,405,235 | 9/1983 | Rossiter | 356/246 |
| 4,753,776 | 6/1988 | Hillman . | |
| 4,756,884 | 7/1988 | Hillman et al. . | |
| 4,761,381 | 8/1988 | Blatt . | |
| 4,762,798 | 8/1988 | Deutsch . | |
| 4,963,498 | 9/1990 | Hillman . | |
| 5,064,282 | 11/1991 | Curtis | 356/40 |
| 5,088,816 | 2/1992 | Tomioka et al. | 356/246 |

FOREIGN PATENT DOCUMENTS

| | | | |
|---|---|---|---|
| 116243 | 9/1980 | Japan | 356/246 |
| 2228800 | 12/1988 | United Kingdom . | |

*Primary Examiner*—Richard A. Rosenberger
*Attorney, Agent, or Firm*—Cox & Smith Incorporated

[57] ABSTRACT

A method and apparatus for making cuvettes. The cuvette comprises two optically transparent liquid impermeable plastic sheets. A third "sticky" sheet is inserted between the two transparent plastic sheets and the three sheets are pressure sealed together. The thickness of the "sticky" sheet defines the optical pathlength of the turbid media. The "sticky" sheet has cut outs defining the contour of an optical chamber, inlet port and vent port.

11 Claims, 3 Drawing Sheets

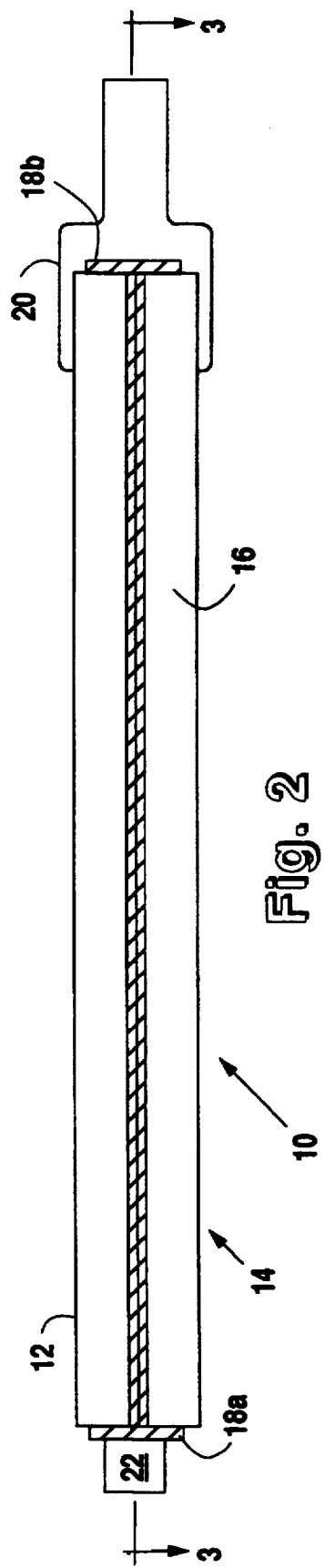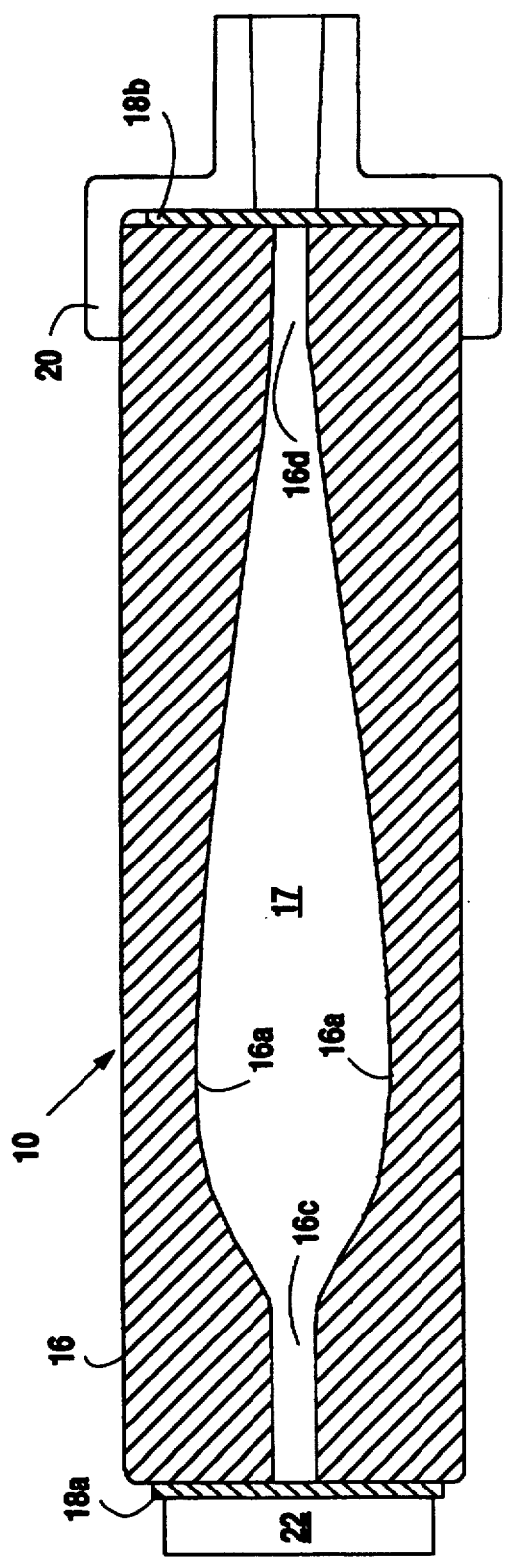

DISPOSABLE OPTICAL CUVETTE

The work leading to the present invention was partially supported by SBIR Grant No. 1 R43 HL47273-01. The United States Government may hold rights in any patent issuing therefrom.

BACKGROUND OF THE INVENTION

1. Field of the Invention

The present invention relates to a new and improved optical cuvette. The cuvette of the present invention allows the making of improved spectrophotometric measurements in turbid media such as whole blood.

2. BACKGROUND OF THE INVENTION

The present invention relates to a disposable optical cuvette #or making spectrophotometric measurements in turbid media such as whole blood and a method of constructing the cuvette. Spectrophotometric measurements on certain compounds that absorb light strongly or those on turbid samples that scatter light appreciably, require a relatively short optical pathlength. The optical pathlength from one cuvette to the next must be consistent for spectrophotometric measurements to be accurate. Therefore, the method of construction of cuvettes must be uniformly controlled.

Numerous approaches have been taken to resolve the problem of uniformly constructing cuvettes with a short optical pathlengths. U.S. Pat. 4,753,776 to Hillman discloses a cuvette for separating plasma from blood by filtration to resolve the light scattering problem when measuring whole blood. The reason Hillman separates whole blood into plasma and red blood cells is that red blood cells scatter and absorb light and could adversely affect a measurement of either reflected or transmitted light of a diagnostic test relying on either of these measurement techniques.

The optical distance through the sample of interest, i.e., width dimension, in an optical chamber is the optical pathlength, and the amount of light absorbed by the sample is directly proportional to the optical pathlength. Therefore, the optical pathlength varies from one cuvette to another, varying degrees of light absorbance and light scattering will induce error in spectrophotometric measurements.

Attempts to control light scattering by utilizing a defined volume chamber is disclosed in U.S. Pat. Nos. 4,963,498 and 4,756,884 to Hillman, et al. Hillman, et al., rely upon injection molding of a multi-layered cuvette to define the optical chamber. The multi-layered cuvette is then ultrasonically welded together. Assembling Hillmanz's cuvette is a multi-step operation involving repeated ultrasonic bonding of each surface to its adjoining surface. This particular construction technique limits the lower limit of the optical pathlength due to the shrinkage found in the component parts of a multi-layer cuvette after injection molding. Hillman, et al., disclose an optical pathlength to be equal to or greater than 180 micrometers.

Another approach to control the optical pathlength is disclosed by U.S. Pat. No. 4,585,561 to Thornton, et al. This patent discloses a cuvette with two chambers. One chamber holds the sample of interest, i.e., whole blood and a second is an over-flow chamber. The first chamber that holds the sample of interest has an optical pathlength of 0.2 cm. That lower optical pathlength is achieved by vacuum forming a portion of the optical chamber. The over-flow chamber is an attempt to remove air bubbles from the sample. Those air bubbles will cause inconsistent readings when making spectrophotometric measurements on whole blood.

The general type and construction of cuvettes disclosed in '498 and '561 are also disclosed in U.S. Pat. Nos. 3,690,836, 4,761,381 and 4,762,798. All the patents have as one of their objectives the measurement of turbid media by optical means, all with varying degrees of success. Whole blood both scatters and absorbs light making optical measurements difficult at best. Past methods have unsuccessfully attempted to remedy this problem by injection molding, and vacuum forming sample volume cavities, thereby controlling the optical pathlength.

The problem of producing a consistent, very low optical pathlength through turbid media, such as whole blood, has not been solved.

SUMMARY OF INVENTION

The technique the present invention uses to achieve a consistent, very short optical pathlength in making spectrophotometric measurements is to optimize Beer's law. Beer's law in part states, the shorter the optical pathlength, the less the absorption of light. By reducing the optical pathlength and thus the optical density of the sample, the present invention enables one skilled in the art of spectrophotometry to make accurate measurements directly on whole blood without the need for dilution or hemolysis. The reduced concentration of whole blood also has the effect of reducing reflections of light due to the reduced concentration of red blood cells in the whole blood sample.

To implement Beer's law the present invention utilizes a thin film with an adhesive coating on both sides, i.e., a double-back "sticky" sheet. The thickness of the "sticky" sheet corresponds to the desired optical pathlength as required to implement Beer's law and is preferably in the range of 80 to 130 micrometers. The medial portions of the "sticky" sheet is pattern die stamped to the peripheral configuration of a cuvette. Then the "sticky" sheet is mounted to a similarly shaped liquid impermeable, transparent plastic sheet. Once mounted, the excess material formed by the die cut pattern is removed from the sticky sheet leaving only the required material to form the desired optical chamber and required pathways connecting the optical chamber with vent and inlet ports. A second substantially rectangular liquid impermeable transparent plastic sheet is placed over the first sheet. The residual portion of the "sticky" sheet thus resides between the first and second sheets of transparent plastic. The completed assembly is flat pressed, uniformly sealing both sides of the "sticky" sheet to the juxtaposed surfaces of the two transparent plastic sheets, thus defining a cuvette of desired very short optical pathlength.

If desired, an adaptor is inserted over one end of the individual cuvette to accommodate a syringe that will hold the sample of interest. An alternate adaptor would be one that is sufficiently tapered to accommodate the tapered portion of the syringe, commonly called a Luer adaptor. A vent plug permeable to air but impermeable to red blood cells is installed over the other end of the cuvette. An alternate vent plug that is not air permeable may be used instead of a preferred air permeable vent plug. However, this vent plug must be punctured to allow air to escape during tile filling of a cuvette. With or without the aforementioned adaptors, the cuvette is ready to use with an optical pathlength completely determined by the very low thickness of a double backed "sticky" sheet.

An alternate assembly process would use large substantially rectangular transparent liquid impermeable plastic sheets and a similar size "sticky" sheet concurrently to produce a plurality of individual cuvettes.

A further advantage of this invention will be readily apparent to those skilled in the art from the following detailed description, taken in conjunction with the annexed sheets of drawings, a preferred embodiment of the invention.

BRIEF DESCRIPTION OF DRAWINGS

FIG. 2 is a side elevational view of a cuvette assembled from the sheet elements of FIG. 1.

FIG. 3 is a sectional view taken on the plane 3—3 of FIG. 2.

DETAILED DESCRIPTION OF PREFERRED EMBODIMENTS

Figure 1:
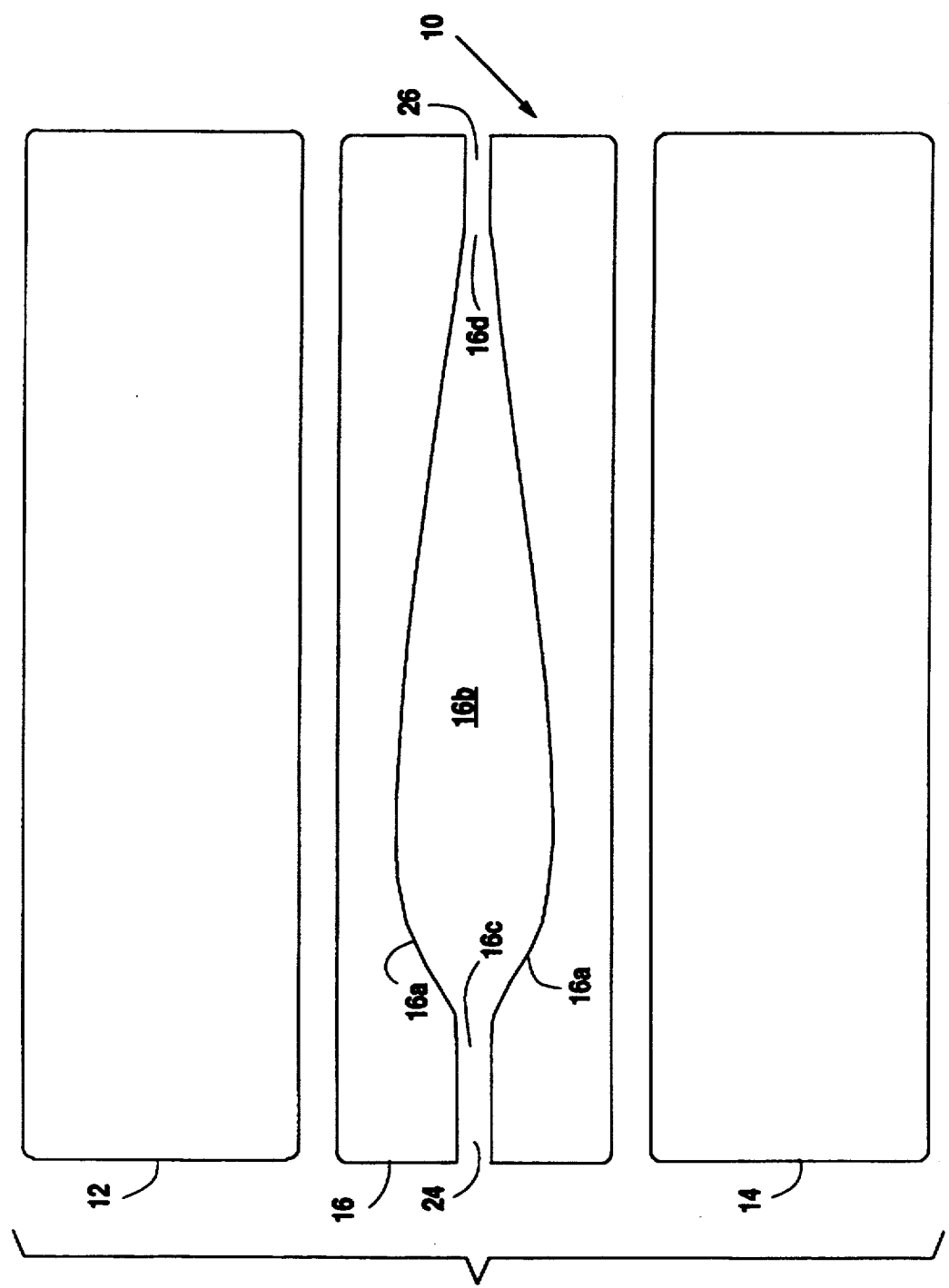
FIG. 1 is a plan view of the three sheet elements from which a cuvette embodying this invention is assembled.

Referring to FIG. 1, an optical cuvette constituting a preferred embodiment of the present invention is shown generally at 10. Optical cuvette 10 comprises two transparent, liquid impermeable, substantially flat sheets 12 and 14 (FIG. 1). Those sheets are preferably made from optically transparent plastic, sold under the trade mark Lexan ®. Although the sheets are shown to be in substantially rectangular form for the preferred embodiment, the actual shape may be varied. Sheets 12 and 14 are adhesively secured together by a double back "sticky" sheet 16 sold under the trade mark Arcare ® 7840 and 3M ® 415 having a thickness corresponding to a desired optical pathlength for the cuvette, which, for purposes of the present explanation is preferably 80 to 130 micrometers thick.

The method of construction of cuvette 10 involves the pattern die cutting of the double-backed "sticky" sheet 16 as indicated at 16a, to provide a readily removable piece 16b, having the desired contour of an optical chamber 17 and pathways 16c and 16d, connecting an inlet port 26 and a vent port 24 to the optical chamber 17.

The "sticky" sheet 16 is then applied to one of the flat sheets 12 and 14, the removable die cut piece 16b is then peeled off. The other flat sheet is then applied over the sticky sheet 16. The remainder of the sticky sheet 16 will hold the two transparent flat streets together providing a liquid tight seal and will form an optical chamber of defined volume, shape, and optical pathlength.

Preferably foam gaskets 18a and 18b are adhesively attached to each end of cuvette 10. The foam gaskets 18a and 18b are air permeable but impermeable to red blood cells. On one end of cuvette 10, there is attached a preferred syringe needle adapter 20, commonly called a Luer adapter. The Luer adapter 20 is preferably form fitted to the one end of the cuvette 10. A porous polyethylene vent plug 22 is preferably adhesively attached to the foam gasket 18a at the end of the cuvette opposite to the Luer tapered adapter 20.

FIG. 2 shows a cuvette 10 completely assembled with all of the preferred embodiments of the present invention. The transparent plastic sheets 12 and 14 are mounted to the "sticky" sheet 16. The foam gasket 18a and 18b are adhesively attached to each end of the cuvette 10. The Luer adapter 20 is form fitted to one end of cuvette 10. The porous polyethylene vent plug 22 is adhesively attached to the foam gaskets 18a at the end of cuvette 10 opposite to the Luer adapter 20.

The preferred manufacturing process of the present invention enables a plurality of cuvettes to be produced from two large sheets of transparent plastic, such as Lexan ®. The plastic sheet may be of commercial variety provided it is substantially flat on both surfaces. A double-backed "sticky" sheet that is the same area as the plastic sheets is preferably patterned die-cut to produce a plurality of adjacent configurations corresponding to "sticky" sheet 16. Each configuration may be perforatedly joined to the adjacent configuration. This large patterned sheet of double-backed "sticky" sheet is adhesively attached to a surface of one of the large plastic sheets. The cut-out portions are removed from the "sticky" sheet. The second large sheet of transparent plastic is placed over the first sheet containing the "sticky" sheet. The sticky sheet, which determines the optical pathlength of all cuvettes formed, therefore resides between the first and second sheets of transparent plastic. The entire assembly is then flat pressed to uniformly seal both large plastic sheets to sides of the "sticky" sheet surfaces.

The assembly is then preferable die-cut to produce a plurality of individual cuvettes 10. Foam gaskets 18a and 18b are placed over each end of each cuvette 10. A vent plug 22 is secured to one end of the cuvette 10. A Luer tapered adapter 20 is secured, by form fitting to the other end of the cuvette 10. The results of the preferred manufacturing process are a ready-to-use disposable optical cuvette 10 with a consistent very short optical pathlength.

Figure 4:
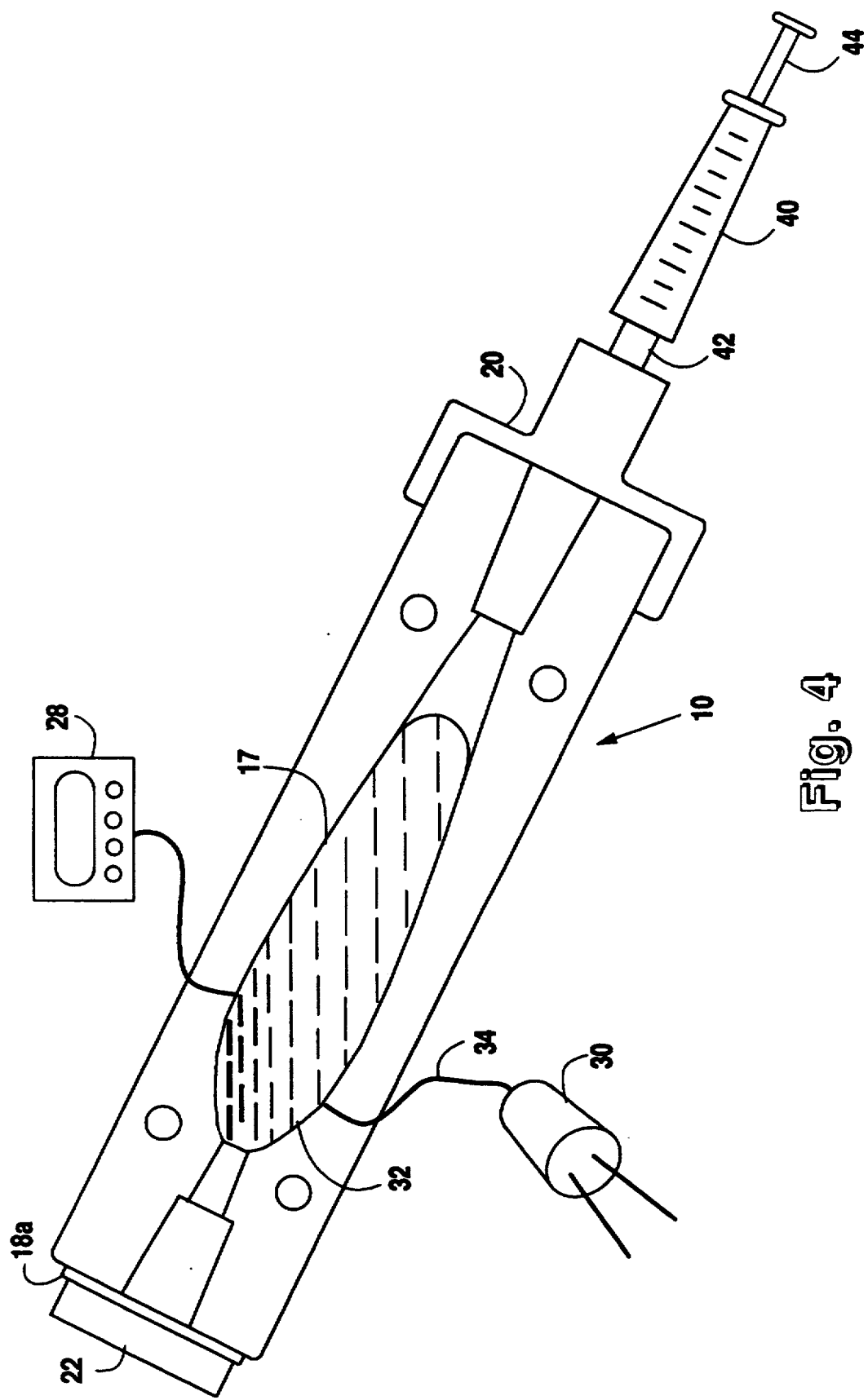
FIG. 4 is an environmental illustration of a cuvette of FIG. 1.

The utilization of cuvette 10 follows the standard procedures found in the diagnostic environment, as schematically shown in FIG. 4. A syringe 40 is filled with a sample of interest, such as whole blood. The syringe's Luer tip 42 is inserted into the Luer tapered adapter 20, and the plunger 44 of the syringe is depressed. That action forces the fluid out of the syringe and into the optical chamber 17 of cuvette 10. Simultaneously air is forced out through the vent plug 22, leaving only liquid wholly contained within the chamber 17 cuvette 10.

Normally, to make a spectrophotometric measurement on a turbid sample 32, a light source 30 provides the necessary light beam 34 that passes through the sample 32 and is received by the detector 28. The distance the light travels through the turbid media sample 32 is the optical pathlength. Once the optical pathlength through the sample 32 has been established, the detector 28 is calibrated to the optical pathlength. Unfortunately, optical pathlengths vary from one cuvette to another. This varying optical pathlength will disturb the calibration of the detector 28 and thereby produce a detected measurement that is in error. If particles, such as red blood cells are present, scattering of the light will result, but such light scattering can be minimized if the optical pathlength is reduced to the range of 80 to 130 micrometers.

The present invention solves the problem of producing cuvettes with consistent very short optical pathlengths by using a combination of two techniques. The first technique is to minimize the optical pathlength to a range of 80 to 130 micrometers. The second technique is to set the optical pathlength by using a "sticky" sheet 16 that is of uniform thickness and to construct the cuvette by the methods above mentioned. Making spectrophotometric measurements utilizing the present invention will yield more consistent measurements due to low absorption of light, minimal light scattering by turbid samples, and consistent optical pathlengths.

The invention now being fully described, it will be apparent to one of ordinary skill in the art that many changes and modifications can be made thereto without departing from the spirit or scope of the invention as set forth herein.

I claim:

1. A method for producing an optical cuvette comprising:

forming a cut-out for defining an optical chamber of selected volume and shape in a plastic film having adhesive layers in both sides thereof and having a selected thickness that defines an optical pathlength perpendicular to the longitudinal axis of said film; and assembling two optically transparent substantially flat sheets of plastic with said plastic film disposed intermediate said transparent sheets in a sandwich relationship such that said adhesive layers on the sides of said plastic film secure said two transparent flat sheets together to provide a liquid tight seal and wherein the resulting assembly comprises an optical cuvette having an optical chamber of selected volume and shape, and an optical pathlength equal to the thickness of said plastic film.

2. A method for producing an optical cuvette as set forth in claim 1 wherein the step of forming the cut-out for defining an optical chamber comprises die cutting a portion of said plastic film to form a removable piece defining a selected shape and size for said optical chamber.

3. A method of producing an optical cuvette as set forth in claim 2 wherein said step of assembly comprises:

removing said die cut piece before adhesively securing said plastic film to one of said two optically transparent flat sheets; and adhesively securing the other side of said plastic film to the other of said two optically transparent flat sheets.

4. A method for producing an optical cuvette as set forth in claim 2 wherein said cut-out in said plastic film defines an optical chamber, a vent port, an inlet port, and a pathway connecting said one optical chamber and said ports.

5. A method for producing an optical cuvette as set forth in claim 4 further comprising:

securing a vent plug formed of a material that is impermeable to aqueous liquids over said vent port.

6. A method for producing an optical cuvette as set forth in claim 5 wherein said vent plug is formed of a material that is permeable to air.

7. A method for producing an optical cuvette as set forth in claim 2 further comprising:

providing said two optically transparent, substantially flat sheets and said plastic film in a size permitting the production of a plurality of cuvettes;

pattern die cutting a plurality of adjacent configurations in said plastic film, each configuration having at least one cut-out defining an optical chamber having an optical pathlength perpendicular to the longitudinal axis of said plastic film;

adhesively securing said plastic film to one of said two optically transparent, substantially flat sheets;

adhesively securing the other side of said plastic film to the other of said two optically transparent, substantially flat sheets thereby forming a sandwich assembly wherein said plastic film is sandwiched between said two optically transparent flat sheets and wherein the thickness of said plastic film defines the optical pathlength of the cuvette; and cutting the sandwich assembly to produce a plurality of individual cuvettes.

8. The method of producing an optical cuvette as set forth in claim 7 further comprising:

flat pressing the sandwich assembly to uniformly seal said two optically transparent substantially flat sheets to both sides of said plastic 9. A method for producing an optical cuvette as set forth in claim 8 wherein said configurations are perforatedly joined to adjacent configurations.

10. A method for producing an optical cuvette as set forth in claim 8 wherein said cut-outs defining said optical chambers are removed after said plastic film is adhesively secured to one of said two optically transparent substantially flat sheets, but before said plastic film is adhesively secured to the other of said two optically transparent substantially flat sheets.

11. A method for producing an optical cuvette as set forth in claim 8 wherein said cut-outs defining said optical chambers are removed before said plastic film is first adhesively secured to one of said two optically transparent substantially flat sheets.

* * * * *